United States Patent
Thornton

(10) Patent No.: US 6,752,828 B2
(45) Date of Patent: Jun. 22, 2004

(54) ARTIFICIAL VALVE

(75) Inventor: Sally C. Thornton, Marlborough, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 25 days.

(21) Appl. No.: 10/115,557

(22) Filed: Apr. 3, 2002

(65) Prior Publication Data

US 2003/0191525 A1 Oct. 9, 2003

(51) Int. Cl.$^7$ .................................................. A61F 2/06
(52) U.S. Cl. .................. 623/1.24; 623/2.12; 623/23.68
(58) Field of Search .............................. 623/1.24, 1.26, 623/23.64, 23.68, 1.36, 2.12, 2.13, 2.14, 2.15, 2.16, 2.17, 2.18, 2.19

(56) References Cited

U.S. PATENT DOCUMENTS

| | | | | |
|---|---|---|---|---|
| 3,589,392 A | * | 6/1971 | Meyer | 137/846 |
| 3,903,548 A | | 9/1975 | Nakib | 3/1.5 |
| 4,218,782 A | | 8/1980 | Rygg | 3/1.5 |
| 4,406,022 A | | 9/1983 | Roy | 3/1.8 |
| 4,580,568 A | | 4/1986 | Gianturco | 128/345 |
| 4,643,732 A | | 2/1987 | Pietsch et al. | 632/2 |
| 4,851,001 A | | 7/1989 | Taheri | 623/2 |
| 4,863,467 A | | 9/1989 | Bokros | 623/2 |
| 5,032,128 A | | 7/1991 | Alonso | 623/2 |
| 5,080,668 A | | 1/1992 | Bolz et al. | 623/2 |
| 5,147,389 A | | 9/1992 | Lane | 623/2 |
| 5,156,619 A | | 10/1992 | Ehrenfeld | 623/1 |
| 5,163,953 A | | 11/1992 | Vince | 623/2 |
| 5,358,518 A | | 10/1994 | Camilli | 623/2 |
| 5,360,401 A | | 11/1994 | Turnland | 604/96 |
| 5,413,599 A | | 5/1995 | Imachi et al. | 623/2 |
| 5,476,471 A | | 12/1995 | Shifrin et al. | 606/151 |
| 5,607,465 A | * | 3/1997 | Camilli | 623/1.24 |

(List continued on next page.)

FOREIGN PATENT DOCUMENTS

| | | | |
|---|---|---|---|
| EP | 0 732 087 A1 | 9/1996 | |
| EP | 0856300 | 8/1998 | ............ A61F/2/24 |
| FR | 2728457 | 6/1996 | ............ A61F/2/06 |
| WO | WO 00/67679 | 11/2000 | ............ A61F/2/24 |
| WO | WO 01/19285 | 3/2001 | ............ A61F/2/06 |
| WO | WO 01/54625 A1 | 8/2001 | |
| WO | WO 01/56500 | 8/2001 | ............ A61F/2/01 |
| WO | WO 02/41764 | * 5/2002 | |

Primary Examiner—Corrine McDermott
Assistant Examiner—Thomas J Sweet
(74) Attorney, Agent, or Firm—E.J. Brooks & Associates, PLLC

(57) ABSTRACT

Method and apparatus implementing and using techniques for controlling flow in a body lumen, including use of an implantable medical device. The device includes a membrane implantable in a body lumen and invertably deformable between a first position and a second position. The membrane is invertible in response to the direction of fluid flow through the lumen and can be deformable by fluid flow in the body lumen.

23 Claims, 15 Drawing Sheets

U.S. PATENT DOCUMENTS

| | | | | |
|---|---|---|---|---|
| 5,609,598 | A | 3/1997 | Laufer et al. | 606/142 |
| 5,769,780 | A | 6/1998 | Hata et al. | 600/36 |
| 5,810,847 | A | 9/1998 | Laufer et al. | 606/142 |
| 5,855,601 | A | 1/1999 | Bessler et al. | 623/2 |
| 5,919,224 | A | 7/1999 | Thompson et al. | 623/1 |
| 6,015,431 | A | 1/2000 | Thornton et al. | 623/1 |
| 6,027,525 | A | 2/2000 | Suh et al. | 623/1 |
| 6,110,201 | A | 8/2000 | Quijano et al. | 623/2.1 |
| 6,126,686 | A | 10/2000 | Badylak et al. | 623/1.24 |
| 6,162,245 | A | 12/2000 | Jayaraman | 623/1.15 |
| 6,168,614 | B1 | 1/2001 | Andersen et al. | 623/1 |
| 6,168,619 | B1 | 1/2001 | Dinh et al. | 623/1.13 |
| 6,200,336 | B1 | 3/2001 | Pavenik et al. | 623/1.15 |
| 6,241,763 | B1 | 6/2001 | Drasler et al. | 623/1.24 |
| 6,287,334 | B1 * | 9/2001 | Moll et al. | 623/1.24 |
| 6,299,637 | B1 | 10/2001 | Shaolian et al. | 623/1.24 |
| 6,315,793 | B1 | 11/2001 | Bokros et al. | 623/1.24 |
| 6,319,281 | B1 | 11/2001 | Patel | 623/2.3 |
| 6,328,727 | B1 * | 12/2001 | Frazier et al. | 604/500 |
| 6,334,873 | B1 | 1/2002 | Lane et al. | 623/2.14 |
| 6,440,164 | B1 | 8/2002 | DiMatteo et al. | 623/1.24 |
| 6,458,153 | B1 | 10/2002 | Bailey et al. | 623/1.24 |
| 6,503,272 | B2 | 1/2003 | Duerig et al. | 623/1.24 |
| 6,508,833 | B2 | 1/2003 | Pavenik et al. | 623/1.15 |
| 6,572,652 | B2 | 6/2003 | Shaknovich | 623/2.11 |
| 6,602,286 | B1 * | 8/2003 | Strecker | 623/1.24 |
| 2001/0021872 | A1 | 9/2001 | Bailey et al. | 623/1.24 |
| 2001/0039450 | A1 * | 11/2001 | Pavcnik et al. | 623/1.24 |
| 2003/0023300 | A1 | 1/2003 | Bailey et al. | 623/1.13 |
| 2003/0069635 | A1 | 4/2003 | Cartledge et al. | 623/2.13 |
| 2003/0069646 | A1 | 4/2003 | Stinson | 623/23.7 |
| 2003/0130726 | A1 | 7/2003 | Thorpe et al. | 623/1.24 |
| 2003/0130729 | A1 | 7/2003 | Paniagua et al. | 623/2.11 |

* cited by examiner

ARTIFICIAL VALVE

FIELD OF THE INVENTION

This invention relates to medical devices for use in a body lumen.

BACKGROUND

A venous valve functions to prevent retrograde flow of blood and allow only antegrade flow of blood to the heart. Referring to FIG. 1A, a healthy venous valve 12 is illustrated in a vessel 10. The valve is bicuspid, with opposed cusps 14. In the closed condition, the cusps 14 are drawn together to prevent retrograde flow (arrow 16) of blood. Referring to FIG. 1B, if the valve is incompetent, the cusps 14 do not seal properly and retrograde flow of blood occurs. Incompetence of a venous valve is thought to arise from at least the following two medical conditions: varicose veins and chronic venous insufficiency.

SUMMARY

This invention relates to medical devices for use with a body lumen. In one aspect, the invention features a medical device including a membrane implantable in a body lumen and invertably deformable between a first position and a second position. The membrane is invertible in response to the direction of fluid flow through the lumen and can be deformable by fluid flow in the body lumen. The membrane can be invertable relative to a radial direction of the body lumen. The membrane can be reversibly deformable between the first position and the second position.

Implementations can include one or more of the following. The membrane can define a portion of a cone, and can include an anchoring element adjacent a vertex of the cone. The membrane can include an anchoring element configured to embed within the body lumen, or alternatively configured to penetrate through the body lumen. The anchoring element may be, for example, a loop or a barb. The membrane can be formed of a polymer, for example, a polyurethane, polyethylene or fluoroplastic.

In another aspect, the invention features a medical system. The system includes multiple membranes, each membrane implantable in a body lumen and invertably deformable between a first position and a second position. Each membrane is invertible in response to the direction of fluid flow through the lumen.

Implementations of the system can include one or more of the following. The membranes can be symmetrically implantable in the body lumen. Each membrane can be invertable relative to a radial direction of the body lumen and can be deformable by fluid flow in the body lumen. At least one membrane can be reversibly deformable between the first position and the second position. At least one membrane can define a portion of a cone and can include an anchoring element adjacent a vertex of the cone. At least one membrane can include an anchoring element configured to embed within the body lumen or alternatively configured to penetrate through the body lumen. The anchoring element can be, for example, a loop or a barb. At least one membrane can be formed of a polymer, for example, a polyurethane, polyethylene or fluoroplastic.

In another aspect, the invention features a method. The method includes positioning at least one membrane in a body lumen, each membrane invertably deformable between a first position and a second position. Each membrane is invertible in response to the direction of fluid flow through the lumen.

Implementations of the method can include one or more of the following. The method can include positioning multiple membranes in the body lumen. The multiple membranes can be positioned symmetrically in the body lumen. The method can include penetrating an anchoring element of the at least one membrane through the body lumen or, alternatively, embedding an anchoring element of the at least one membrane into the body lumen.

In another aspect, the invention features a method of controlling flow in a body lumen. The method includes invertably deforming a membrane between a first position and a second position, the membrane being invertible in response to the direction of fluid flow through the lumen. Implementations can include one or more of the following. The membrane in the second position and a portion of the body lumen can define a cavity. Deformation of the membrane can be relative to a radial axis of the body lumen. The membrane can be deformable by fluid flow in the body lumen. The membrane in the first position and the membrane in the second position can be approximately mirror images of each other. The method can further include invertably deforming a plurality of membranes.

Embodiments may have one or more of the following advantages. One or more invertible membranes, which can function as artificial valve cusps, can be implanted at a treatment site using a catheter. As such, implantation is minimally invasive and avoids surgery and the possibility of the inherent complications. The membrane is fabricated from a polymer such as a polyurethane, polyethylene or fluoroplastic, which materials are more easily accessible than a natural tissue excised from an animal, and can be manufactured with consistency and efficiency that could be more difficult or more expensive using a natural tissue.

Other features, objects, and advantages of the invention will be apparent from the description and drawings, and from the claims.

DETAILED DESCRIPTION

Figure 1A:
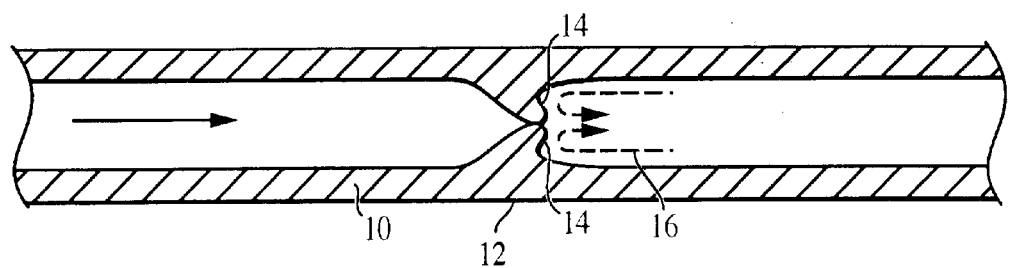
FIGS. 1A and 1B are illustrations of a venous valve and an incompetent venous valve, respectively.
Figure 1B:
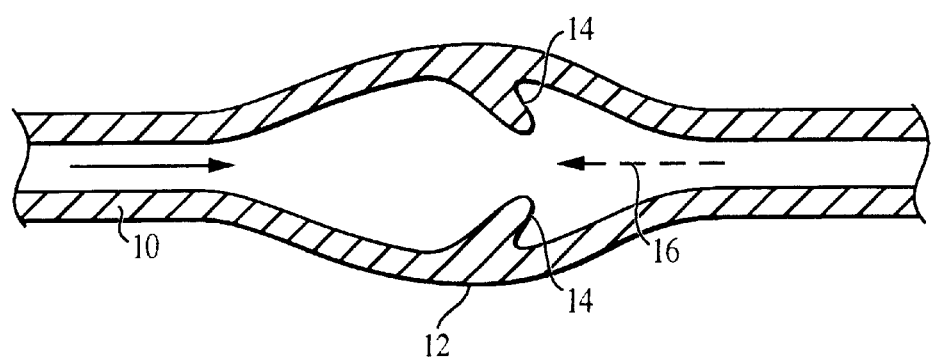

Referring to FIGS. 2A–2C through FIG. 4, a pair of artificial valve cusps 30 are illustrated positioned within a vessel 46, e.g., a vein. Cusps 30 can be positioned upstream or downstream relative to an incompetent venous valve, such as the valve shown in FIG. 1B. Each artificial valve cusp 30 includes at least one anchoring element 38 attached to an invertable portion 42, here, an approximately triangular, flexible membrane. Anchoring element 38 is generally configured to hold invertable portion 39 at a desired location in vessel 46. For example, anchoring element 38 can embed itself within a wall 44 of vessel 46, or penetrate through the wall to secure cusp 30 to the vessel. Invertable portion 42 is capable of deforming between a first position and a second position, e.g., between an opened condition and a closed position, in response to flow of body fluid in vessel 46 to allow or to reduce the flow in the vessel.

Figure 2C:
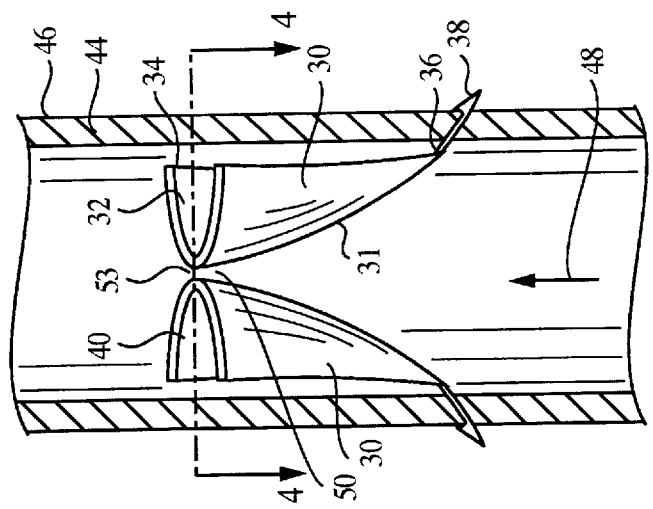
FIGS. 2A, 2B, and 2C are partial perspective views of an embodiment of a valve cusp.
Figure 2B:
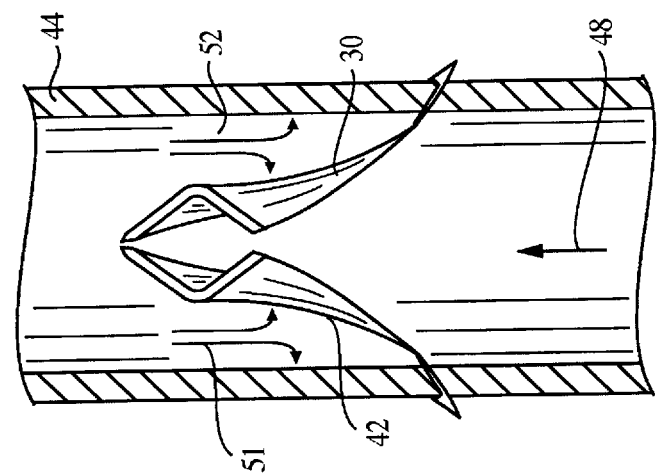
Figure 2A:
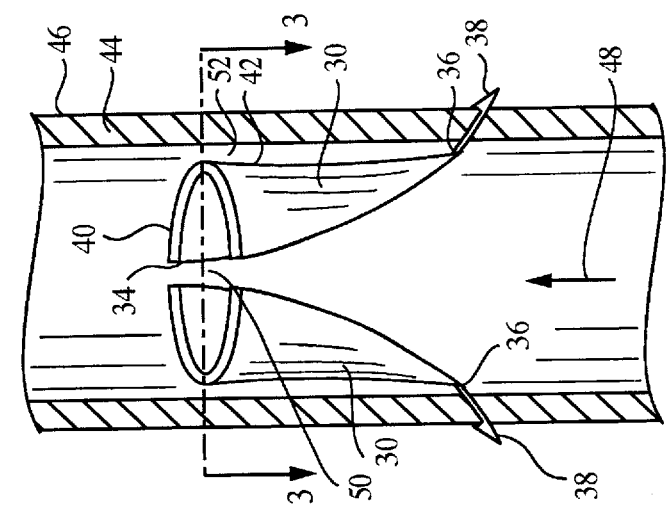
Figure 3:
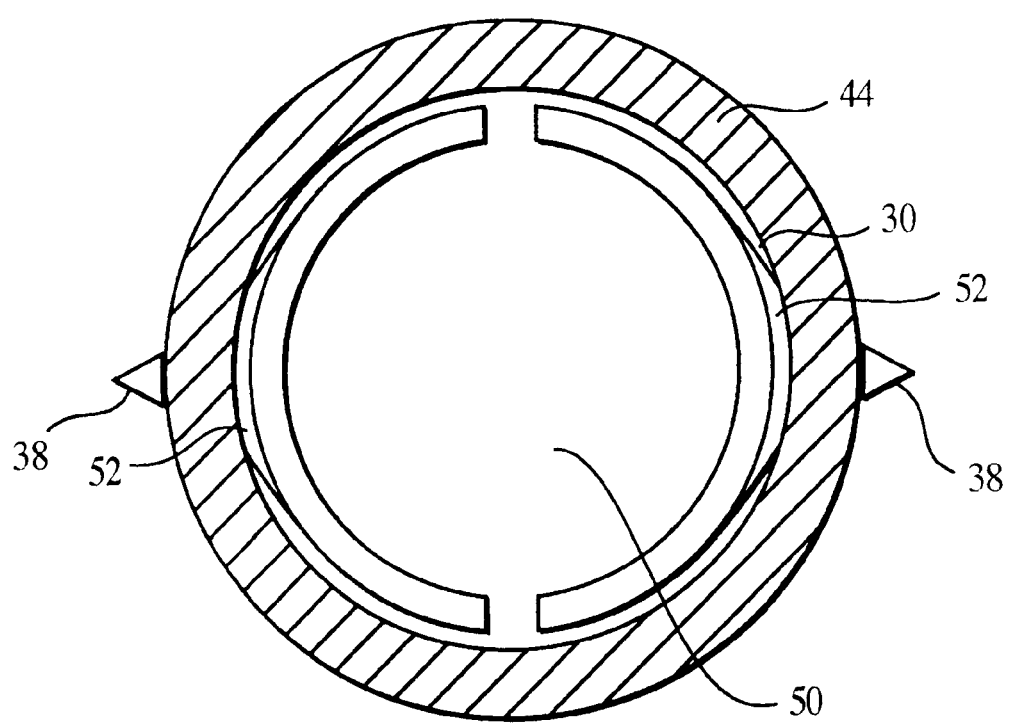
FIG. 3 is a cross-sectional view of the valve cusp of FIG. 2A, taken along line 3—3.

Referring particularly to FIG. 2A and FIG. 3, the cusps 30 are shown in a first position in which each cusp 30 forms an approximate semi-cone, such that an opening 50 is formed by the curved surfaces of the cusps 30. The opening 50 allows antegrade flow of a fluid through the vessel in the direction indicated by arrow 48. The membranes of invertable portions 42 are relatively thin and can conform closely to the vessel wall 44 to maximize the size of opening 50. However, each cusp 30 is also held slightly away from the wall 44 of the vessel 46 by the anchoring element 38, such that a gap 52 is formed between the invertable portion 42 and the wall 44.

Figure 4:
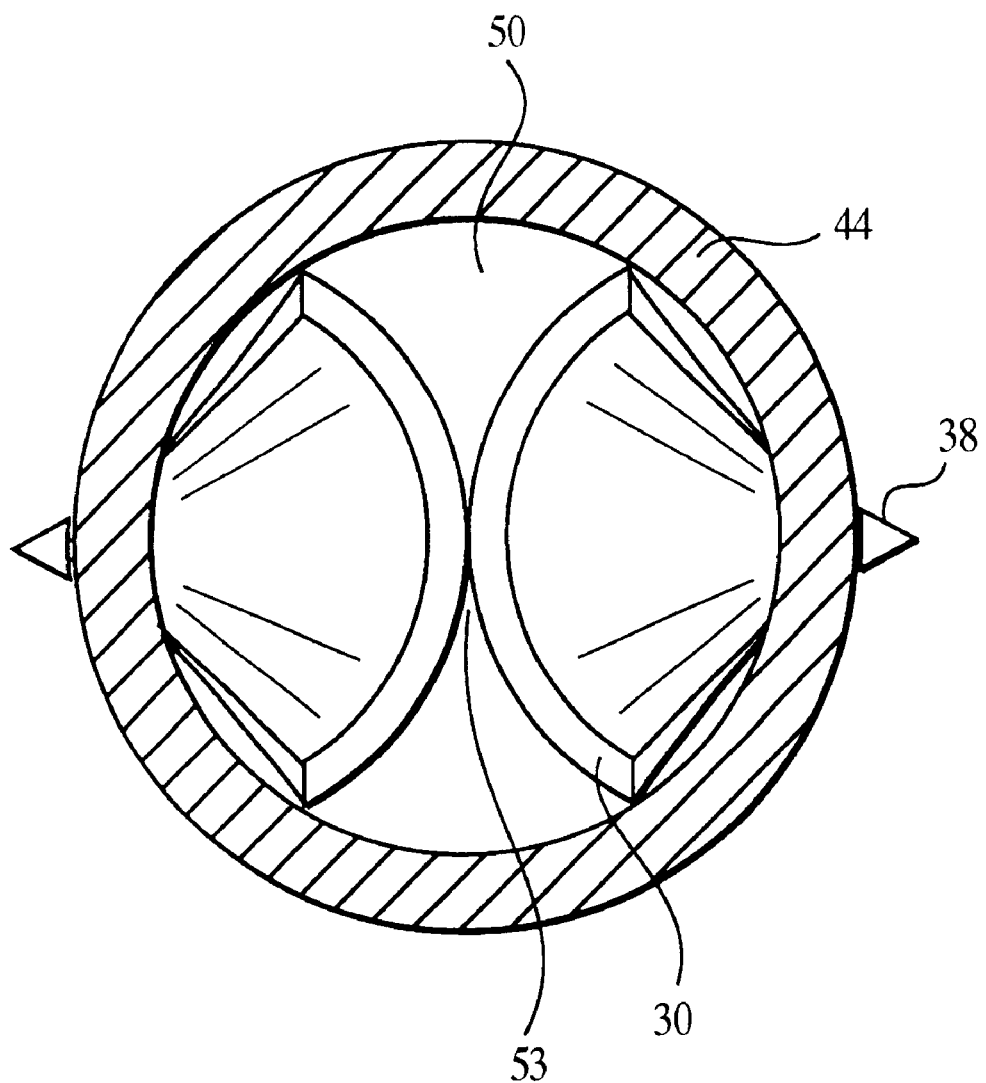
FIG. 4 is a cross-sectional view of the valve cusp of FIG. 2C, taken along line 4—4.

Referring particularly to FIG. 2B, retrograde flow of fluid (arrows 51) in the vessel can accumulate in the gap 52 and exert pressure on the invertable portion 42 of the cusp 30. Since invertable portion 42 is flexible, it can deform under the exerted pressure and invert to form another approximate semi-cone, as shown in FIG. 2C. That is, each cusp 30 forming a first semi-cone in the first position can invert or flip relative to a radial axis of vessel 46 to form a second semi-cone that is approximately the mirror image of the first semi-cone. As the interior 32 of the second semi-cone accumulates retrograde flowing fluid, pressure is exerted on the interior of cusp 30, causing the cusp to move away from the wall 44 of the vessel. As a result, the space 53 between the two cusps 30 narrows, the size of opening 50 decreases, and fluid flow through the vessel and past the cusps is reduced (FIG. 4).

The cusps 30 can remain in the second position until antegrade fluid flow exerts sufficient pressure on the surface of cusps 30 opposite interior 32 and inverts the cusps to the first position. Thus, cusps 30 provide an artificial valve that automatically responds to the flow of fluid or pressure changes in vessel 46.

Figure 5A:
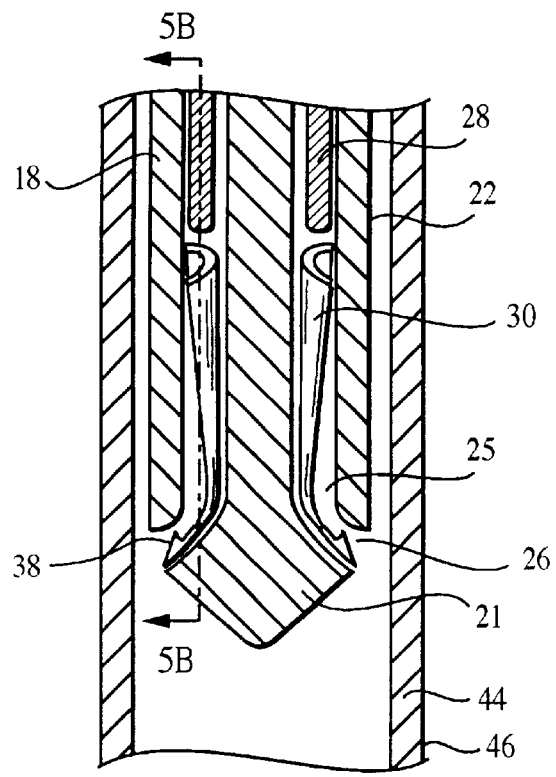
FIGS. 5A, 5B, 5C, 5D and 5E are schematic views of an embodiment of a method for implanting a valve cusp.
Figure 5B:
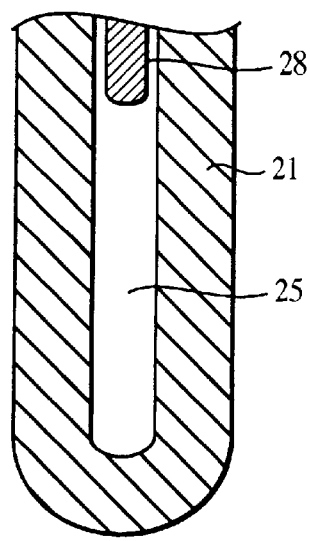

FIGS. 5A to 5E show one method of positioning cusps 30 at a treatment site in vessel 46 using a catheter 18 that may be delivered into the vessel 46 percutaneously. The catheter 18 is generally adapted for delivery through the vessel 46, e.g., using a guidewire. Catheter 18 includes a long, flexible body having a central portion 21, and a retractable sheath 22 over the central portion. Referring particularly to FIG. 5B, a cross-sectional view of FIG. 5A taken along line 5—5, two grooves 25 are formed on either side of the central portion 21, and a push rod 28 is positioned inside each of the grooves 25. Each cusp 30 is positioned in a groove 25 in a compacted state and held in place by the retractable sheath 22 until delivery at the treatment site.

Figure 5C:
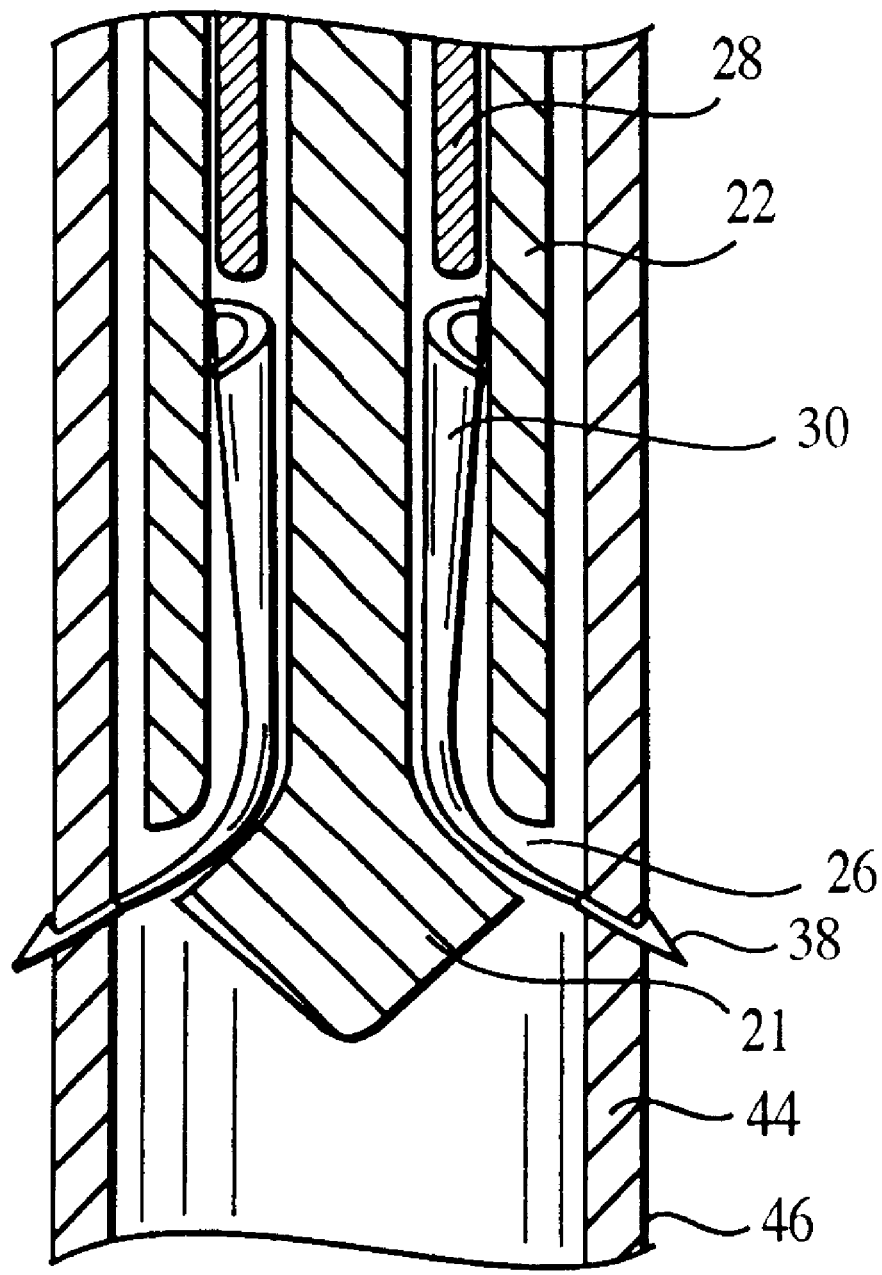

Catheter 18 can be delivered to the treatment site using endoprosthesis delivery techniques, e.g., by tracking an emplaced guidewire with central lumen 101. At the treatment site, the retractable sheath 22 is retracted proximally to form an opening 26 at the end of each groove 25. Referring particularly to FIG. 5C, push rods 28 are used to push each cusp 30 distally toward the opening 26 to push the anchoring element 38 out of the opening 26. The cusps 30 are pushed out of the openings 26 until the anchoring elements 38 secure the cusps 30 to the wall 44 of the vessel 46. For example, the anchoring elements 38 can embed within the wall 44 or penetrate the wall 44 and secure to the exterior of the vessel 46.

Figure 5D:
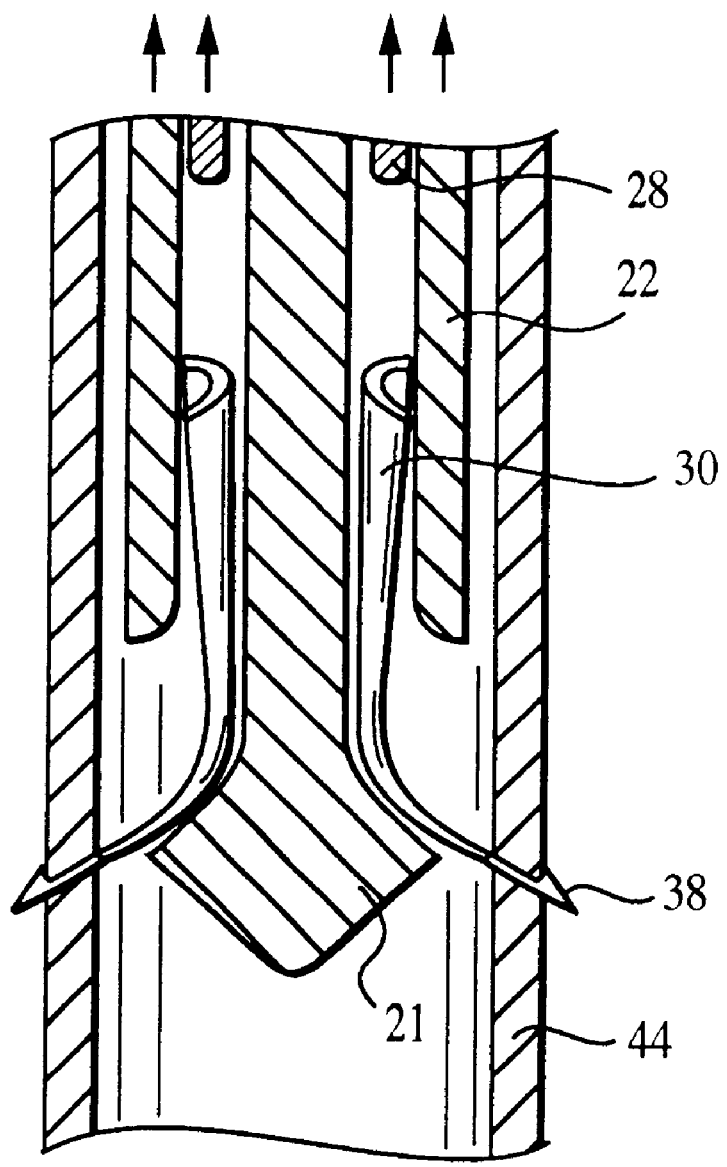
Figure 5E:
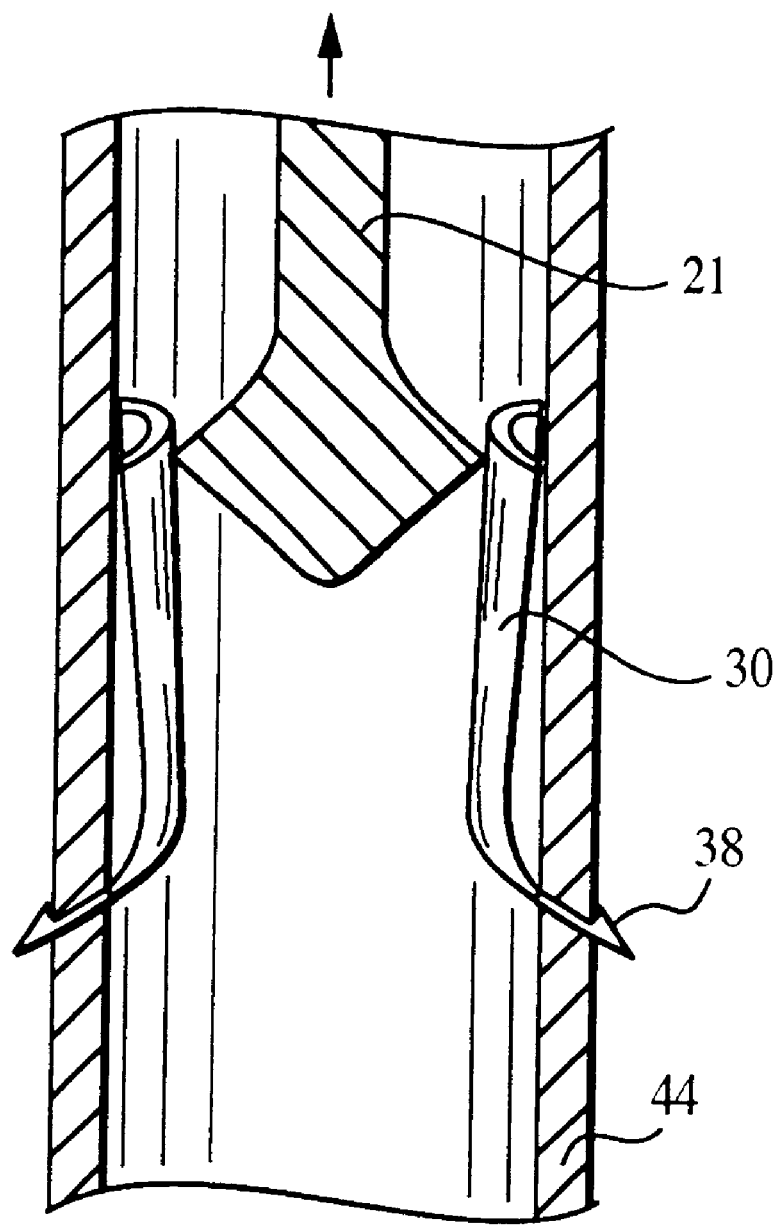

After each cusp 30 is secured to the vessel 46, the retractable sheath 22 is retracted to fully expose the cusps 30 (FIG. 5D). The central portion 21 is then pulled proximally past the flexible (and deflectable) cusps 30 and retracted from the vessel 46 (FIG. 5E). The cusps 30, now secured to the wall 44, can deform between the first and second positions, as described above.

Cusps 30 are preferably made of a biocompatible material capable of reversible deformation as described above. Each cusp 30 can be formed from a thin, flexible material, such as a polyurethane, polyethylene or fluoroplastic, for example, polytetrafluoroethylene (PTFE). Invertable portion 42 can be formed of one or more materials. For example, invertable portion 42 may include an edge portion that is relatively more flexible or more compliant than another portion of the invertable portion to help the edges meet and seal when the cusps 30 are in the second position. Cusps 30 can include a radiopaque material, such as a polymer including a radiopacifier, e.g., tantalum metal or bismuth oxychloride, for positioning and monitoring the cusps.

Similarly, anchoring element 38 is preferably biocompatible. The anchoring element 38 can be formed of a relatively rigid material, such as a polymer having suitable hardness, for example, acrylonitrile-butadiene-styrene (ABS). Other materials can be used, such as metals (e.g., tantalum, tungsten or gold), alloys (e.g., stainless steel or Nitinol), and ceramics. Anchoring elements 38 can include a radiopaque material for positioning and monitoring cusps 30. The anchoring element can be embedded in the invertible portion or fixed to a surface of the invertible portion with, for example, adhesive.

Other Embodiments

In other embodiments, any number of cusps can be anchored to the wall 44 of the vessel 46 to function as a valve for preventing retrograde flow of blood through the blood vessel 46.

Figure 6A:
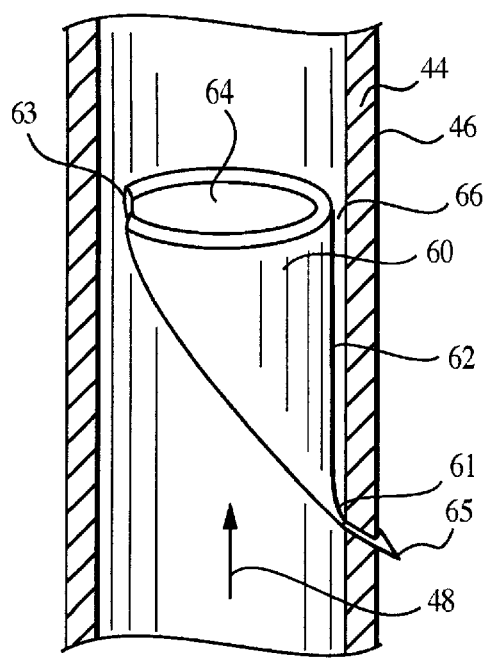
FIGS. 6A and 6B are partial perspective views of an embodiment of a valve cusp.
Figure 6B:
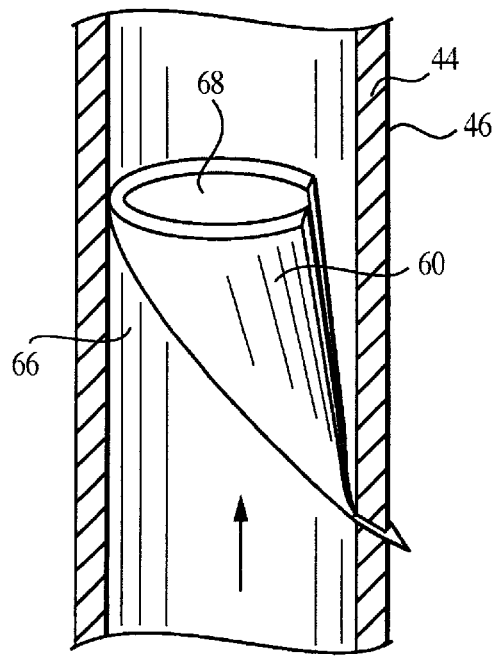

Referring to FIGS. 6A and 6B, a single cusp 60 can be used. The cusp 60 can be transported to the treatment site and anchored to the wall 44 of a vessel 46 in the same manner as described above using a catheter. In a first position, the cusp 60 forms an approximate semi-cone, with the edges 63 of the semi-cone facing the wall 44 opposite from where the cusp 60 is anchored to the wall 44. The interior of the cone forms a channel 64 allowing fluid flow past the cusp 60. The anchoring element 65 holds the cusp 30 slightly away from the wall 44 such that a gap 66 is formed between the cusp 60 and the wall 44. Retrograde flowing fluid can accumulate in the gap 66 and exert pressure on the cusp 60, deforming the cusp 60 and widening the gap 66 until the pressure on the cusp 60 inverts the cusp. Referring particularly to FIG. 6B, in an inverted position the cusp 60 forms an approximate cone with the wall 44 and accumulates retrograde flowing fluid in a sack 68 formed by the interior of the cone. Accumulated fluid can exert pressure on the cusp 60, causing the cusp 60 to move away from the wall 44. As a result, the space 66 between the cusp 60 and the wall 44 opposite the anchoring element narrows, until the cusp 60 touches the wall 44, in a second position as shown. In the second position, flow is reduced past the cusp 60 relative to the flow when the cusp 60 was in the first position. The cusp 60 remains in the second position until pressure exerted on the cusp 60 by the antegrade flow of fluid is sufficient to invert the cusp 60 to the first position.

Figure 7A:
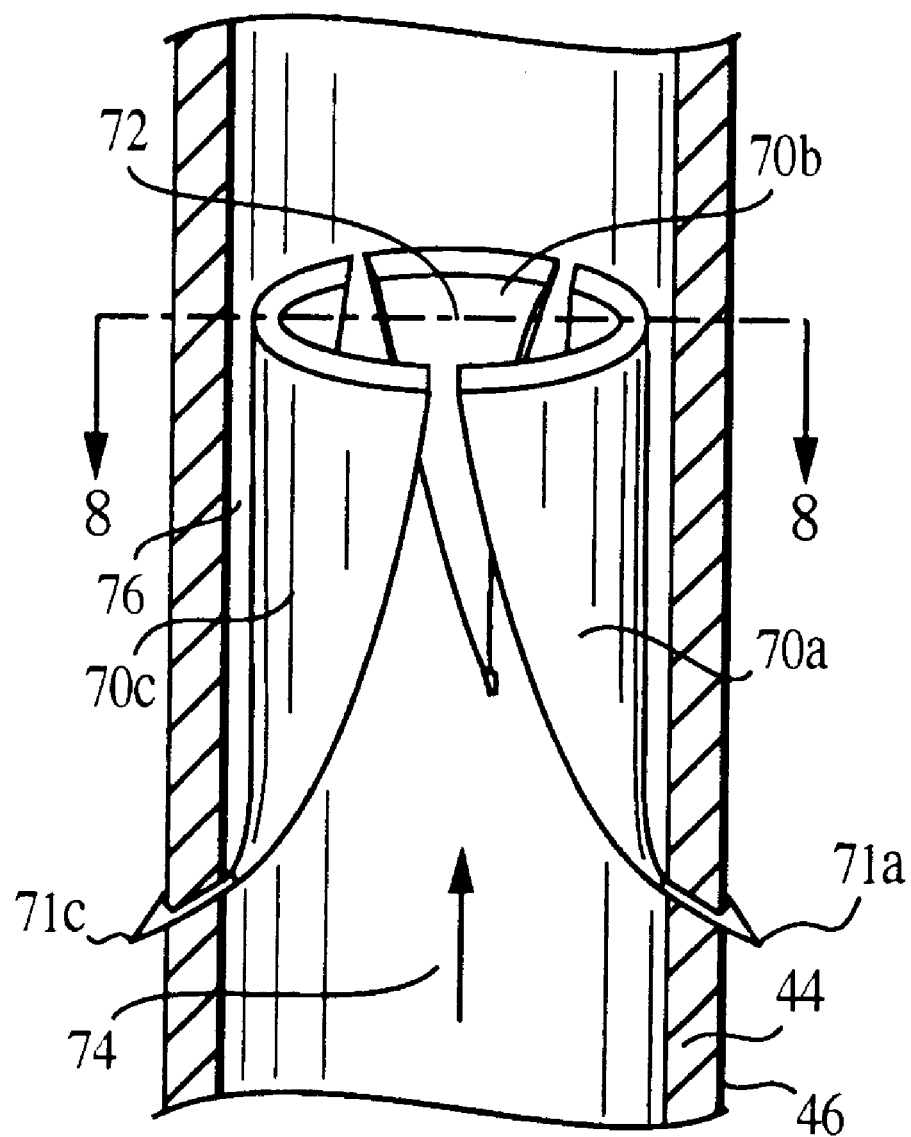
FIGS. 7A and 7B are partial perspective views of an embodiment of a valve cusp.
Figure 7B:
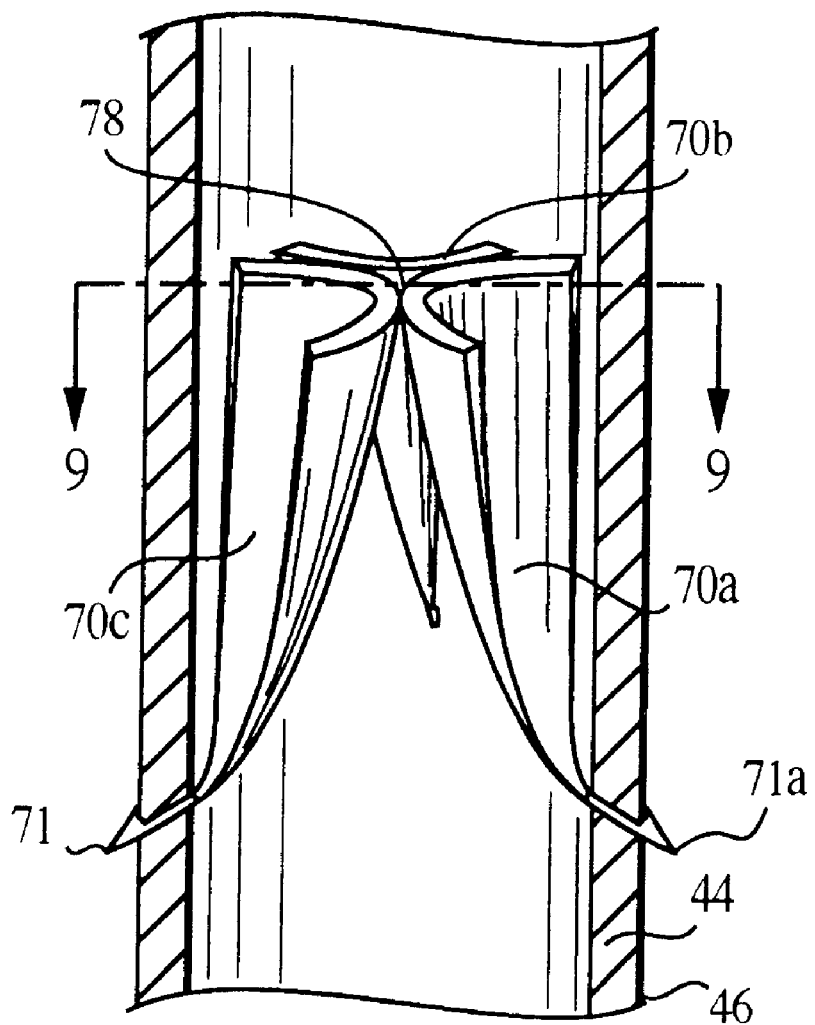
Figure 8:
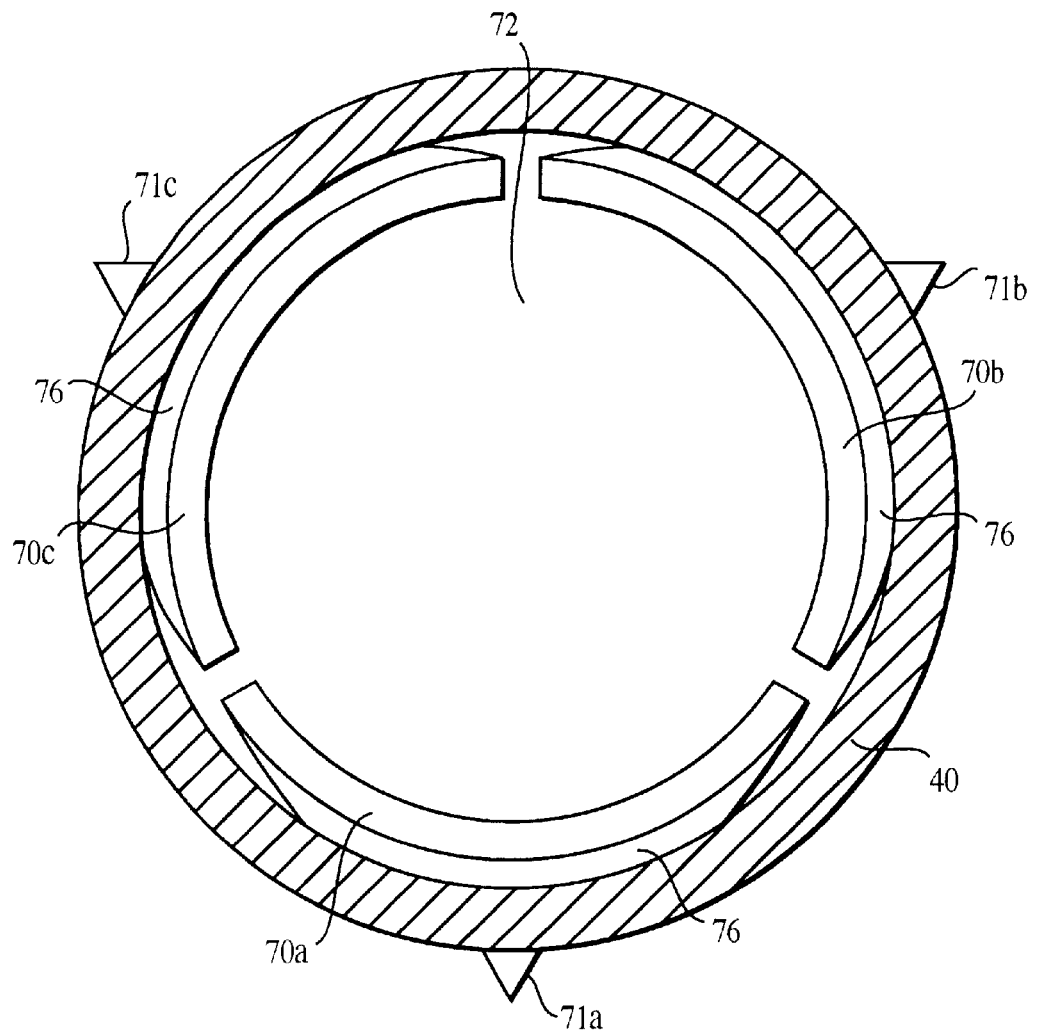
FIG. 8 is a cross-sectional view of the valve cusp of FIG. 7A, taken along line 8—8.

Referring to FIGS. 7A–7B, three cusps 70a–70c can be symmetrically secured to the wall 44 of a vessel 46 in a similar manner as described above. Referring particularly to FIG. 7A, the cusps 70a–70c are shown in first position that does not substantially impede flow of a fluid through the vessel 46. As shown in FIG. 8, the surfaces of the cusps 70a–70c conform to the wall 44 of the vessel 46, allowing a substantial opening 72 for flow past the cusps 70a–70c. Each cusp 70a–70c is held away from the wall 44 by anchoring elements 71a–71c, such that a gap 76 is formed between each cusp and the wall 44. As described above, retrograde flowing fluid accumulates in the gap 76 and exerts pressure on the cusp 70, causing the cusp to deform away from the wall 44, until the cusps invert.

Figure 9:
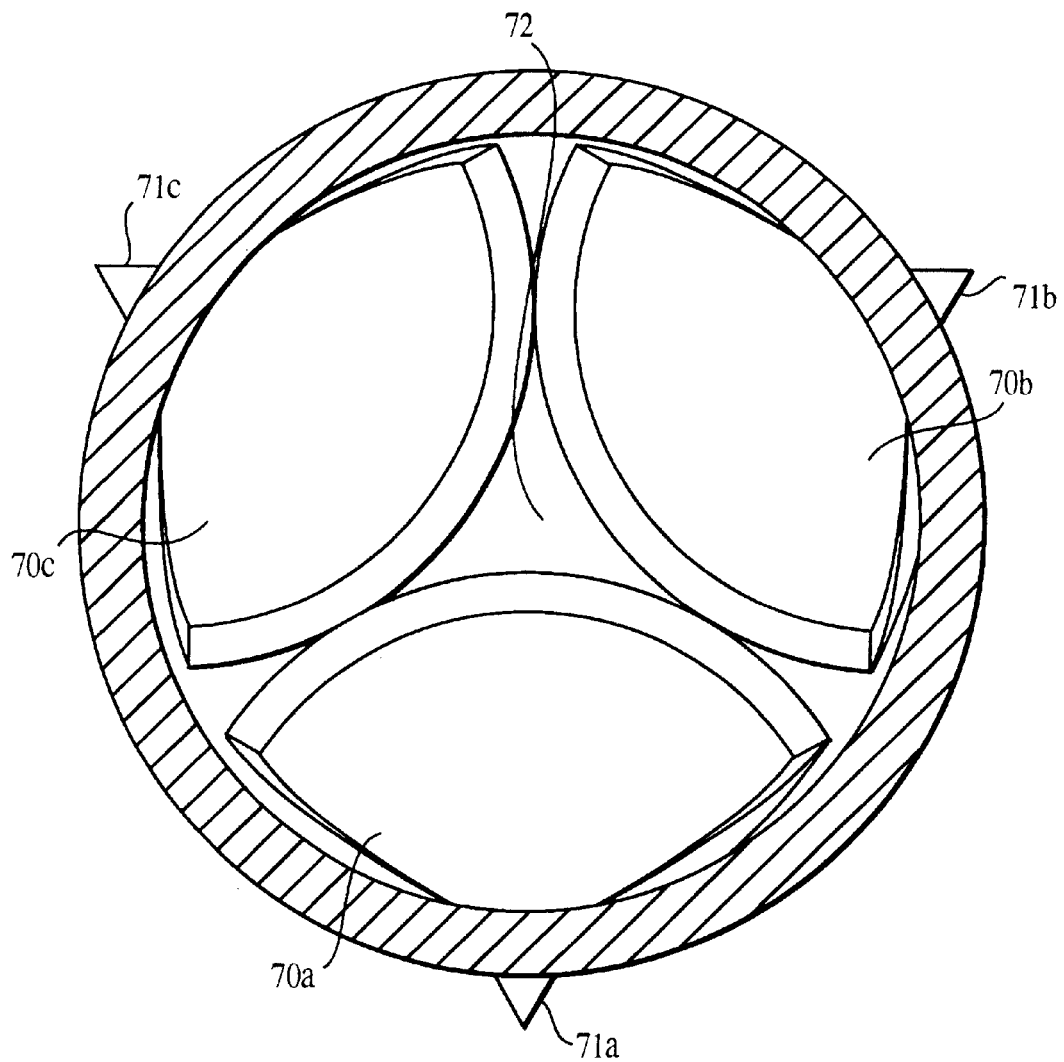
FIG. 9 is a cross-sectional view of the valve cusp of FIG. 7A, taken along line 9—9.

Referring particularly to FIG. 7B, in an inverted position the interior of each cusp 70a–70c accumulates retrograde flowing fluid. Exerting pressure on the cusps causes them to move toward one another, until the cusps 70a–70c meet in a second position and reduce flow past the cusps 70a–70c relative to the when the cusps 70a–70c are in the first position. Referring to FIG. 9, the opening 72 is significantly reduced, thus restricting the fluid flow. The cusps 70a–70c remain in the second position until pressure exerted on the cusps 70a–70c by antegrade flow of fluid inverts the cusps to the first position.

Figure 12:
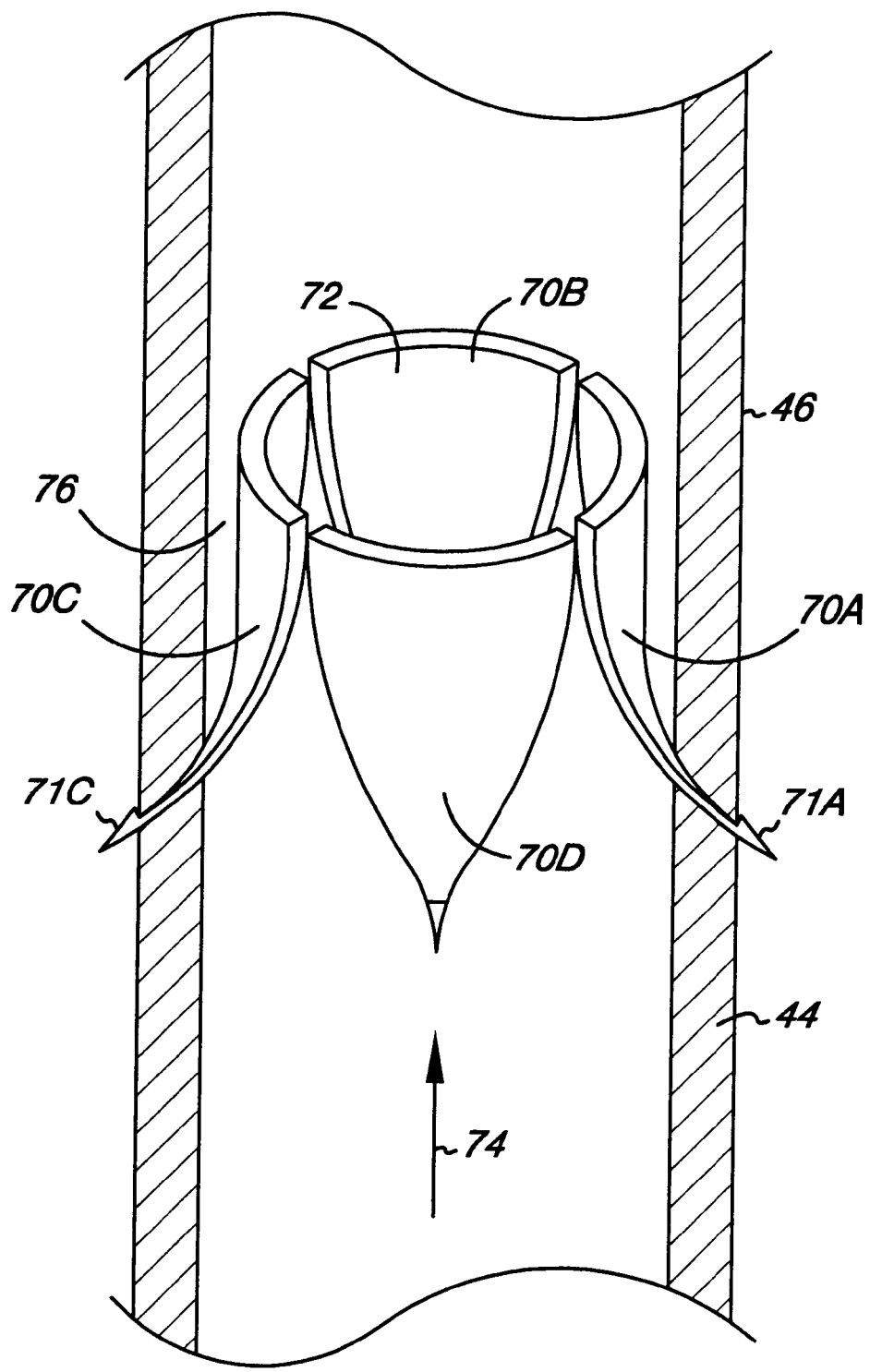
FIG. 12 is a partial perspective view of an embodiment of a valve cusp.

Although the embodiments above describe a device having one to three cusps, any number of cusps can be used to prevent retrograde flow through a vessel. FIG. 12 provides one example of four cusps, or membranes, used to prevent retrograde flow through a vessel. The cusps can be arranged symmetrically as shown, or can be arranged in any other configuration. Although the embodiments described above include cusps of similar size and configuration, cusps of differing sizes and configurations can be used in conjunction with each other.

Figure 10:
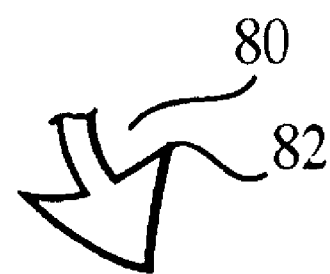
FIG. 10 is a partial perspective view of an embodiment of an anchoring element.
Figure 11:
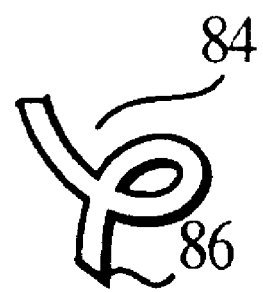
FIG. 11 is a partial perspective view of an embodiment of an anchoring element.

The anchoring element can take a number of different forms that permit the end of the cusp to penetrate the wall of a blood vessel and restrain the end of the cusp from re-entering the vessel. For example, the anchoring element can be a barb element, as shown in the embodiments described above. Alternatively, the anchoring element can be a T-hook device 80 as shown in FIG. 10, wherein T-hook 80 penetrates the wall of a vessel and hooks 82 prevent the anchor from re-entering the vessel. In another embodiment, the anchoring element can define a loop 84, as shown in FIG. 11, wherein the looped end 86 prevents the anchor from re-entering the vessel.

In other embodiments, a cusp can include more than one anchoring element. A cusp can have other polygonal configurations. For example, a generally rectangular cusp can be secured to a vessel using two anchoring elements adjacent to two corners of the cusp. The cusp can form a semi-cylinder.

Other embodiments are within the scope of the following claims.

What is claimed is:

1. A medical system, comprising:
a plurality of frameless membranes, the plurality of frameless membranes symmetrically implantable in a body lumen and invertibly deformable between a first position and a second position, wherein the membranes are invertible in response to the direction of fluid flow through the lumen.

2. The system of claim 1, wherein the frameless membrane are invertible relative to a radial direction of the body lumen.

3. The system of claim 1, wherein the frameless membranes are deformable by fluid flow in the body lumen.

4. The system of claim 1, wherein at least one frameless membrane defines a portion of a cone.

5. The system of claim 4, wherein at least one frameless membrane includes an anchoring element adjacent a vertex of the cone.

6. The system of claim 1, wherein at least one frameless membrane includes an anchoring element configured to embed within the body lumen.

7. The system of claim 1, wherein at lease one frameless membrane includes an anchoring element configured to penetrate through the body lumen.

8. The system of claim 7, wherein the anchoring element includes a loop.

9. The system of claim 7, wherein the anchoring element includes a barb.

10. The system of claim 1, wherein at least one frameless membrane is formed of a polymer.

11. The system of claim 10, wherein the polymer is a material selected from a group consisting of polyurethanes, polyethylenes and fluoroplastics.

12. The system of claim 1, wherein at least one frameless membrane is reversibly deformable between the first position and the second position.

13. The system of claim 1, comprising two frameless membranes.

14. The system of claim 1, comprising three frameless membranes.

15. The system of claim 1, comprising four frameless membranes.

16. A method comprising:
positioning a plurality of frameless membranes symmetrically in a body lumen, the plurality of frameless membranes invertibly deformable between a first position and a second position,
wherein the plurality of frameless membranes are invertible in response to the direction of fluid flow through the lumen relative to the membranes in the first position.

17. The method of claim 16, wherein at least one of the plurality of frameless membranes includes an anchoring element, the method further including:
penetrating the anchoring element of at least one frameless membrane through the body lumen.

18. The method of claim 16, wherein at least one of the plurality of frameless membranes includes an anchoring element, the method further including:
embedding the anchoring element of at least one frameless membrane into the body lumen.

19. A method of controlling flow in a body lumen, the method comprising:
invertibly deforming a frameless membrane between a first position and a second position, wherein the frameless membrane in the first position and the frameless membrane in the second position are approximately mirror images of each other,
wherein the frameless membrane is invertible in response to the direction of the fluid flow through the lumen.

20. The method of claim 19, wherein the frameless membrane in the second position and a portion of the body lumen define a cavity.

21. The method of claim 19, wherein deformation is relative to a radial axis of the body lumen.

22. The method of claim 19, comprising invertibly deforming a plurality of frameless membranes.

23. The method of claim 19, wherein the frameless membrane is deformable by fluid flow in the body lumen.

* * * * *

UNITED STATES PATENT AND TRADEMARK OFFICE
CERTIFICATE OF CORRECTION

PATENT NO. : 6,752,828 B2
DATED : June 22, 2004
INVENTOR(S) : Sally C. Thornton

It is certified that error appears in the above-identified patent and that said Letters Patent is hereby corrected as shown below:

Column 5,
Line 55, delete "membrane" and insert -- membranes --.

Signed and Sealed this

Fourteenth Day of September, 2004

JON W. DUDAS
*Director of the United States Patent and Trademark Office*